United States Patent
Chattaway et al.

(10) Patent No.: US 11,883,706 B2
(45) Date of Patent: Jan. 30, 2024

(54) FIRE SUPPRESSION BLENDS OF CF3I AND 2-BTP

(71) Applicant: Kidde Technologies, Inc., Wilson, NC (US)

(72) Inventors: Adam Chattaway, Old Windsor (GB); Terry Simpson, Wake Forest, NC (US); Mark P. Fazzio, Wilson, NC (US); Harlan Hagge, Knightdale, NC (US); Paul Papas, West Hartford, CT (US); Marios C. Soteriou, Middletown, CT (US); Eli Baldwin, Knightdale, NC (US); Qing Edda Liu, Wake Forest, NC (US)

(73) Assignee: Kidde Technologies, Inc., Wilson, NC (US)

(*) Notice: Subject to any disclaimer, the term of this patent is extended or adjusted under 35 U.S.C. 154(b) by 0 days.

(21) Appl. No.: 17/798,744

(22) PCT Filed: Feb. 16, 2021

(86) PCT No.: PCT/US2021/018212
§ 371 (c)(1),
(2) Date: Aug. 10, 2022

(87) PCT Pub. No.: WO2021/236184
PCT Pub. Date: Nov. 25, 2021

(65) Prior Publication Data
US 2023/0088487 A1   Mar. 23, 2023

Related U.S. Application Data

(60) Provisional application No. 62/976,801, filed on Feb. 14, 2020.

(51) Int. Cl.
*A62D 1/00* (2006.01)
*C07C 19/14* (2006.01)
*C07C 19/16* (2006.01)

(52) U.S. Cl.
CPC ......... *A62D 1/0092* (2013.01); *A62D 1/0057* (2013.01); *C07C 19/14* (2013.01); *C07C 19/16* (2013.01)

(58) Field of Classification Search
None
See application file for complete search history.

(56) References Cited

U.S. PATENT DOCUMENTS

| 5,759,430 A | 6/1998 | Tapscott et al. |
| 7,153,446 B2 | 12/2006 | Grigg |

(Continued)

FOREIGN PATENT DOCUMENTS

| CN | 103341243 A | 10/2013 |
| EP | 2287271 A | 2/2011 |

(Continued)

OTHER PUBLICATIONS

International Preliminary Report on Patentability for PCT Application No. PCT/US2021/018212, dated Aug. 25, 2022, pages.

(Continued)

*Primary Examiner* — Joseph D Anthony
(74) *Attorney, Agent, or Firm* — Kinney & Lange, P.A.

(57) ABSTRACT

A fire suppression blends of CF3I and 2-BTP with mol ratios from 1:5 and 5:1 are capable of passing peak inerting and sub-inerting tests. The CF3I:2-BTP fire suppression blends can also include carbon dioxide of up to 80% of the fire suppression blend to provide additional cooling.

16 Claims, 4 Drawing Sheets

(56) References Cited

U.S. PATENT DOCUMENTS

| | | |
|---|---|---|
| 7,223,351 B2 | 5/2007 | Sharma et al. |
| 7,597,818 B2 | 10/2009 | Singh et al. |
| 8,492,327 B2 | 7/2013 | Singh et al. |
| 9,309,450 B2 | 4/2016 | Low |
| 9,540,556 B2 | 1/2017 | Minor et al. |
| 9,713,732 B2 | 7/2017 | Mitchell et al. |
| 9,884,946 B2 | 2/2018 | Singh et al. |
| 9,920,230 B2 | 3/2018 | Thomas et al. |
| 9,994,750 B2 | 6/2018 | Singh et al. |
| 10,301,521 B2 | 5/2019 | Sethi et al. |
| 10,335,623 B2 | 7/2019 | Kennoy et al. |
| 10,343,003 B2 | 7/2019 | Baker et al. |
| 10,344,136 B2 | 7/2019 | Bogdan et al. |
| 10,479,747 B2 | 11/2019 | Gregersen et al. |
| 2010/0032610 A1 | 2/2010 | Nappa et al. |
| 2015/0041157 A1* | 2/2015 | Mitchell .............. A62D 1/0092 252/8 |
| 2017/0028240 A1 | 2/2017 | Robin |
| 2018/0016212 A1 | 1/2018 | Singh et al. |
| 2018/0043199 A1 | 2/2018 | Robin |
| 2018/0264303 A1 | 9/2018 | Robin et al. |
| 2018/0318623 A1 | 11/2018 | Richard et al. |
| 2019/0161660 A1 | 5/2019 | Yana Motta et al. |
| 2019/0290946 A1 | 9/2019 | Ribarov et al. |
| 2019/0290950 A1* | 9/2019 | Hagge .................... A62C 35/13 |
| 2019/0290951 A1* | 9/2019 | Hagge .................... A62D 1/005 |

FOREIGN PATENT DOCUMENTS

| | | |
|---|---|---|
| EP | 3546030 A1 | 10/2019 |
| JP | 2018153463 A | 10/2018 |
| WO | 2007144623 A1 | 12/2007 |
| WO | 2014007862 A2 | 1/2014 |
| WO | 2015048604 A1 | 4/2015 |
| WO | 2019036049 A1 | 2/2019 |
| WO | 2019220463 A1 | 11/2019 |

OTHER PUBLICATIONS

International Preliminary Report on Patentability for PCT Application No. PCT/US2021/018217, dated Aug. 25, 2022, 7 pages.
International Search Report and Written Opinion for PCT Application No. PCT/US21/18212, dated Nov. 23, 2021, 10 pages.
International Search Report and Written Opinion for PCT Application No. PCT/US21/18217, dated Nov. 4, 2021, 3 pages.

* cited by examiner

| Prop. (Vol%) | CF3I (Vol%) | 2-BTP (Vol%) | Mol Ratio | Pressure rise (psi) | Comment |
|---|---|---|---|---|---|
| 2.48 | | | | 56.74 | Unsuppressed baseline |
| 2.3 | | 3.25 | | 59.83 | 2-BTP itself will enhance explosion |
| 2.56 | 0.57 | 3 | 1:5 | 56.48 | No higher pressure rise than baseline tests |
| 2.49 | 0.92 | 2.71 | 1:3 | 1.57 | Less pressure rise than baseline tests |
| 2.51 | 1.18 | 2.42 | 1:2 | 0.48 | Less pressure rise than baseline tests |
| 2.52 | 1.8 | 1.8 | 1:1 | 0.34 | Less pressure rise than baseline tests |
| 2.53 | 2 | 1.59 | 5:4 | 0.31 | Less pressure rise than baseline tests |
| 2.52 | 1.58 | 1.99 | 4:5 | 0.49 | Less pressure rise than baseline tests |
| 2.55 | 2.38 | 1.17 | 2:1 | 0.34 | Less pressure rise than baseline tests |
| 2.46 | 3.05 | 0.58 | 5:1 | 0.35 | Less pressure rise than baseline tests |

FIG. 2

| Prop. (Vol%) | CF3I (Vol%) | 2-BTP (Vol%) | Mol Ratio | FIC | Rel. wt to 6% Halon 1301 | Rel. vol to 6% Halon 1301 |
|---|---|---|---|---|---|---|
| 4.05 | 1.12 | 5.48 | 1:5 | 0.82 | 1.32 | 1.19 |
| 3.98 | 1.42 | 5.69 | 1:4 | 0.89 | 1.43 | 1.27 |
| 4.02 | 1.86 | 5.73 | 1:3 | 0.96 | 1.53 | 1.35 |
| 3.96 | 2.52 | 5.01 | 1:2 | 0.98 | 1.51 | 1.31 |
| 4.02 | 3.68 | 3.87 | 1:1 | 1.02 | 1.53 | 1.27 |
| 4.03 | 4.98 | 2.52 | 2:1 | 1.06 | 1.54 | 1.23 |
| 4.02 | 6 | 1.97 | 3:1 | 1.15 | 1.66 | 1.30 |
| 4.01 | 6.49 | 1.29 | 5:1 | 1.15 | 1.64 | 1.26 |

FIG 3

| Prop. (Vol%) | CF3I (Vol%) | 2-BTP (Vol%) | CO2 (Vol%) | Mol Ratio | FIC | Rel. wt to 6% Halon 1301 | Rel. vol to 6% Halon 1301 | Pressure rise (psi) | Comment |
|---|---|---|---|---|---|---|---|---|---|
| 2.48 | | | | | | | | 56.74 | Unsuppressed baseline |
| 2.56 | 0.57 | 3 | | 1:5 | | | | 56.48 | Sub-inerting screening - Not enhance explosion |
| 2.56 | 0.35 | 2.02 | 2.4 | 1:5:6 | | | | 55.26 | Sub-inerting screening - Not enhance explosion |
| 2.49 | 0.31 | 1.51 | 3.57 | 1:5:12 | | | | 1.48 | Sub-inerting screening - Not enhance explosion |
| 3.98 | 0.59 | 3.02 | 7.2 | 1:5:12 | 0.70 | 1.06 | 1.38 | 0.5 | Peak inerting test - Pass |

FIG. 4

FIRE SUPPRESSION BLENDS OF CF3I AND 2-BTP

BACKGROUND

Aircraft cargo compartment fire protection still requires Halon 1301, an ozone depleting substance (ODS) which is being phased out. Production ceased in 1994 in the developed world and in 2010 in developing countries. In addition, the aviation industry is facing "cut-off" dates (i.e. do not use Halon 1301 after this date) and "end dates" (Halon must no longer be used and must be replaced with an alternative agent, including retrofit, after this date). The aviation fire protection community has been searching for a replacement for Halon 1301 for the last 20 years, without success.

A number of options to replace Halon 1301 in cargo compartments have been suggested, including hydrofluorocarbons (HFCs), and 2-bromo-trifluoropropene (2-BTP). None of these is ideal for the following reasons.

HFC's and 2-BTP fail a key performance test (a simulated exploding aerosol canister) in that, if tested at a concentration below the inerting concentration, they can in some circumstances make the explosion worse than if no agent was employed at all. Inert gas and water mist pass this test but the resulting size and weight of the fire protection system has been deemed to be unacceptable by aircraft original equipment manufacturers (OEMs).

A promising Halon replacement agent, trifluoroidomethane or CF3I, does not fail the aerosol can test. However, when tested recently, it failed another test, the bulk load fire test. In this test, the fire load is cardboard boxes filled with shredded paper, which gives rise to deep-seated fire that is difficult to extinguish. $CF_3I$ is less thermally stable than Halon 1301, and the agent decomposed in the "preheat zone", i.e. en route to the fire.

SUMMARY

In one embodiment, a fire suppression blend comprises $CF_3I$ and 2-BTP; wherein a mol ratio of CF3I to 2-BTP in the blend is from 1:5 to 5:1.

In another embodiment, the fire suppression blend comprises CF3I, 2-BTP, and carbon dioxide. The mol ratio of CF3I to 2-BTP in the blend is from 1:5 to 5:1, and up to 80% of the fire suppression blend is carbon dioxide.

BRIEF DESCRIPTION OF THE DRAWINGS

FIG. 2 is a chart showing results of sub-inerting test for CF3I:2-BTP blends.

FIG. 3 is a chart showing results of peak inerting test for CF3I:2-BTP blends.

FIG. 4 is a chart showing sub-inerting and peak inerting test results for CF3I:2-BTP:CO2 blends.

DETAILED DESCRIPTION

Description of Inerting Test

Figure 1:
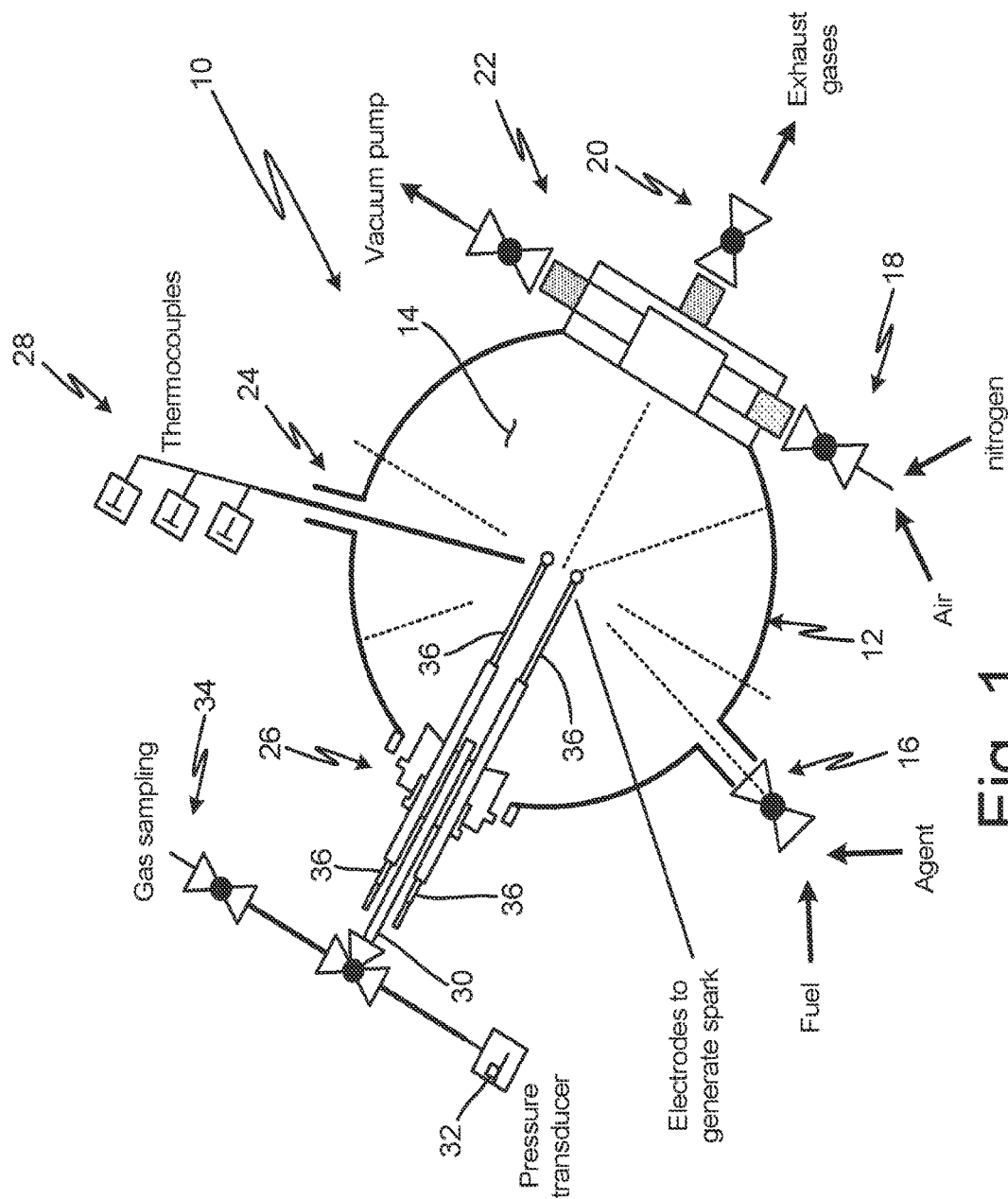
FIG. 1 is a diagram showing an inerting test sphere.

To determine the effectiveness of CF3I:2-BTP fire suppressant blends and CF3I:2-BTP:CO2 fire suppressant blends, two categories of inerting tests were performed: sub-inerting tests and peak inerting tests. Testing was performed against propane-air explosions in 42 liter spherical test vessel 10.

FIG. 1 shows an illustration of spherical test vessel 10, which includes spherical housing 12, interior chamber 14, ports 16, 18, 20, 22, 24, and 26, thermocouples 28, gas probe 30, pressure transducer 32, gas sampler 34, and electrodes 36. Fuel (propane) and fire suppression agents to be tested are introduced into interior chamber 14 of housing 12 through port 16. Air and nitrogen are introduced into the interior of housing through port 18. Exhaust gases generated during a test can be removed through port 20. At the beginning of a test procedure, interior chamber 14 is evacuated through part 22 using a vacuum pump. Thermocouples 28 extend through port 24 to sense temperature within interior vessel 14 during testing. Port 26 provides access to interior chamber for probe 30 and electrodes. Pressure transducer 32 is connected to probe 30 and monitors gas pressure within interior vessel 14 before and during the test. Gas sampler 34 is also is connected to probe 30, and allows sampling of gas within the interior chamber 14 during the test procedure. Electrodes pass through port 26 and extend to the center of interior chamber 14. Electrodes are used to produce a spark to ignite the fuel and initiate the test.

Previous work has defined the stoichiometric (theoretically most explosive) propane-air mixture as 4% propane in air. Therefore, this concentration is used to assess the relative performance of extinguishing agents and blends thereof.

A first step in the procedure for a peak inerting test is to evacuate the sphere. Then, while monitoring pressure transducer 32, propane is added to a pressure of 0.04 atm (i.e. 4% in the final mix), and then the agent or agents are added at the desired concentration. For example, if a blend of 2.5% CF3I and 5% 2-BTP is to be the subject of the peak inerting test, CF3I is added until the pressure reaches 0.065 atm (4% propane+2.5% CF3I). Then, 2-BTP is added until the pressure reached 0.115 atm (4% propane+2.5% CF3I+5% 2-BTP). Finally, air is added to raise the pressure in the sphere to 1.00 atm. Long enough equilibration time or fan mixing is used to ensure that all the gases are mixed homogeneously throughout interior chamber 14 before the test is initiated. At test, the spark is ignited, and the pressure rise is monitored by a data logger. A pressure rise of 1 psi or lower is designated as a pass.

Sub-inerting testing uses 2.5% propane in air, and 0.3-0.5 fractional peak inerting concentration of agent, to predict if the agent/blend would enhance explosion in an exploding aerosol can test. Sub-inerting tests use the same procedure as the peak inerting tests, except 2.5% propane is used in the final mix. A pressure rise that is less than the baseline test pressure rise predicts that the agent (blend) will not generate explosion in the exploding aerosol can test, and therefore passes of the exploding aerosol can test.

Discussions on Synergy

When assessing fire suppression blends, the concept of Fractional Inerting Contribution (FIC) is helpful. This is defined as $$FIC = \sum_{i=1}^{n} \frac{C_i}{IC_i}$$

where Ci is the Concentration of component i, and ICi is the Inerting Concentration of component i.

It has been demonstrated that successful inerting should be attained when FIC is close to 1 (i.e., 0.95+), where effectiveness of the blend is equal to the summation of effectiveness of each component. When a successful inerting test has an FIC less than 1 (0.9 or less), the effectiveness of the blend is higher than the summation of effectiveness of each component. That indicates that a synergy of the components of the blend has a positive effect on suppression efficiency.

CF3I:2-BTP Blends—Sub-Inerting Tests

The objective of the CF3I:2-BTP blends is to add sufficient CF3I to stabilize the 2-BTP against the exploding aerosol can threat. As shown in FIG. 2, the sub-inerting test uses a low fuel concentration (about 2.5% propane) as a screening test for the exploding aerosol can test.

The first data row in FIG. 2 is the unsuppressed baseline test, in which no fire suppression agent is present, which results in a pressure rise of 56.74 psi. This represents the "unsuppressed baseline, against which all of the other test results will be compared to determine efficacy of the fire suppression agents/blend tested. Sub-inerting tests with pressure rise no higher than the unsuppressed baseline pressure rise (56.74 psi) will not enhance explosion at low fuel concentration, and thus should be able to pass aerosol can tests.

The second data row in FIG. 2 is for a test in which only 2-BTP was used as a fire suppression agent. The sub-inerting test result, 59.83 psi pressure rise, is higher than that of unsuppressed baseline test. This means that 2-BTP as the only agent would enhance explosion at low fuel concentration, rather than suppress explosion.

Starting from the third data row of FIG. 2, it shows that CF3I:2-BTP (by mol) higher than 1:5 could stabilize the 2-BTP against the exploding aerosol can threat (pressure rise of blends are all no higher than 56.74 psi). In the third row, the CF3I/2-BTP blend with a 1:5 volume ratio is no higher than the baseline pressure rise of 56.74 psi. For the remainder of the blends shown in FIG. 2, the fourth row shows a pressure rise of 1.57 psi, and the fifth through tenth rows all show pressure rises of less than 1 psi.

CF3I:2-BTP Blends—Peak Inerting Tests

Successful peak inerting test results of CF3I:2-BTP blend of different ratios are shown in FIG. 3. A synergy is shown with the CF3I:2-BTP blend having a mol ratio of 1:5 and FIC of 0.82. Synergy is also shown by a mol ratio of 1:4 by mol and FIC of 0.89. Based on the results shown in FIG. 3, all of the CF3I:2-BTP blends with mol ratios ranging from 1:5 to 5:1 could pass inerting test with 1.3 to 1.6 relative weight to 6% Halon 1301 (peak inerting concentration of Halon 1301), and 1.2 to 1.3 relative volume to 6% Halon 1301.

CF3I:2-BTP:CO2 Blends

Up to 80% $CO_2$ can be added to a CF3I:2-BTP blends having mol ratios from 1:5 to 5:1 to increase volatility of the blend, decrease toxicity, suppress explosion and even increase synergetic effect of the agent. FIG. 4 shows results of sub-inerting and peak inerting tests for example CF3I:2-BTP:CO2 blends with mol ratios of 1:5:6 and 1:5:12. The peak inerting results show FIC of 0.7, indicating the presence of synergy. Both tests shown in FIG. 4 were successful.

In the three-component blend CF3I:2-BTP:CO2 1:5:6 and 1:5:12, sub-inerting tests pressure rise decreased to 55.26 psi and 1.48 psi respectively, comparing to that of CF3I:2-BTP 1:5 which is 56.48 psi. It indicates that CO2 provided extra cooling to CF3I:2-BTP 1:5 and further suppressed sub-inerting explosion beyond the similar function from CF3I. Since CF3I:2-BTP no less than 1:5 could already stabilize the 2-BTP against the exploding aerosol can threat (pressure rise of blends are all no higher than that of unsuppressed baseline test 56.74 psi), CF3I:2-BTP no less than 1:5, with 0-80% CO2 (and preferably 20% to 80% CO2) added for extra cooling in the CF3I:2-BTP:CO2 three-component blend, would also inert the exploding aerosol can threat, and is an option as a fire suppression agent.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A fire suppression blend comprising:
CF3I; and
2-BTP;
wherein a mol ratio for CF3I to 2-BTP is from 1:5 to 5:1.

2. The fire suppression blend of claim 1, wherein a mol ratio of CF3I to 2-BTP is at least 1:3.

3. The fire suppression blend of claim 1, wherein a mol ratio of CF3I to 2-BTP is at least 1:2.

4. The fire suppression blend of claim 1, wherein a mol ratio of CF3I to 2-BTP is at least 1:1.

5. The fire suppression blend of claim 1, wherein a mol ratio of CF3I to 2-BTP is at least 2:1.

6. The fire suppression blend of claim 1, wherein a mol ratio of CF3I to 2-BTP is at least 3:1.

7. The fire suppression blend of claim 1, and further comprising carbon dioxide (CO2).

8. The fire suppression blend of claim 7, wherein carbon dioxide constitutes from 20% to 80% by volume of the fire suppression blend.

9. The fire suppression blend of claim 8, where a mol ratio of CF3I to 2-BTP to CO2 is from 1:5:6 to 1:5:12.

10. A fire suppression blend comprising CF3I, 2-BTP, and CO2, wherein a mol ratio for CF3I to 2-BTP is from 1:5 to 5:1.

11. The fire suppression blend of claim 10, wherein the CO2 constitutes up to 80% by volume of the fire suppression blend.

12. The fire suppression blend of claim 11, wherein a mol ratio of CF3I to 2-BTP is at least 1:3.

13. The fire suppression blend of claim 11, wherein a mol ratio of CF3I to 2-BTP is at least 1:2.

14. The fire suppression blend of claim 11, wherein a mol ratio of CF3I to 2-BTP is at least 1:1.

15. The fire suppression blend of claim 11, wherein a mol ratio of CF3I to 2-BTP is at least 2:1.

16. The fire suppression blend of claim 11, wherein a mol ratio of CF3I to 2-BTP is at least 3:1.

* * * * *